United States Patent [19]

Keller, Jr.

[11] 4,210,151

[45] Jul. 1, 1980

[54] ELECTRONIC PAIN CONTROL WITH SCANNED OUTPUT PARAMETERS

[75] Inventor: John W. Keller, Jr., Miami, Fla.

[73] Assignee: Stimtech, Inc., Minneapolis, Minn.

[21] Appl. No.: 945,974

[22] Filed: Sep. 26, 1978

[51] Int. Cl.$^2$ .............................................. A61N 1/36
[52] U.S. Cl. ................................................... 128/421
[58] Field of Search ................... 128/419 R, 421, 422, 128/423 R, 423 W

[56] References Cited

U.S. PATENT DOCUMENTS

| 2,099,511 | 11/1937 | Caesar | 128/422 |
| 2,350,797 | 6/1944 | Morland et al. | 128/421 |
| 2,381,496 | 8/1945 | Hansell | 128/422 |
| 3,299,892 | 1/1967 | Kendall et al. | 128/421 |
| 3,810,457 | 5/1974 | Bottcher et al. | 128/421 |

Primary Examiner—William E. Kamm
Attorney, Agent, or Firm—Audley A. Ciamporcero, Jr.

[57] ABSTRACT

A first oscillator dictates the pulse duration and frequency of stimulating signals; the oscillator output wave form is coupled to an output amplifier stage, and thence to the patient. A scanning oscillator provides a substantially linear ramp voltage, which in turn controls pulse duration, pulse frequency, and pulse intensity modulators. In turn, these modulators appropriately establish conditions within the first oscillator and the output stage whereby the output parameters are scanned through respective predetermined ranges, thereby periodically achieving optimum stimulating conditions.

9 Claims, 3 Drawing Figures

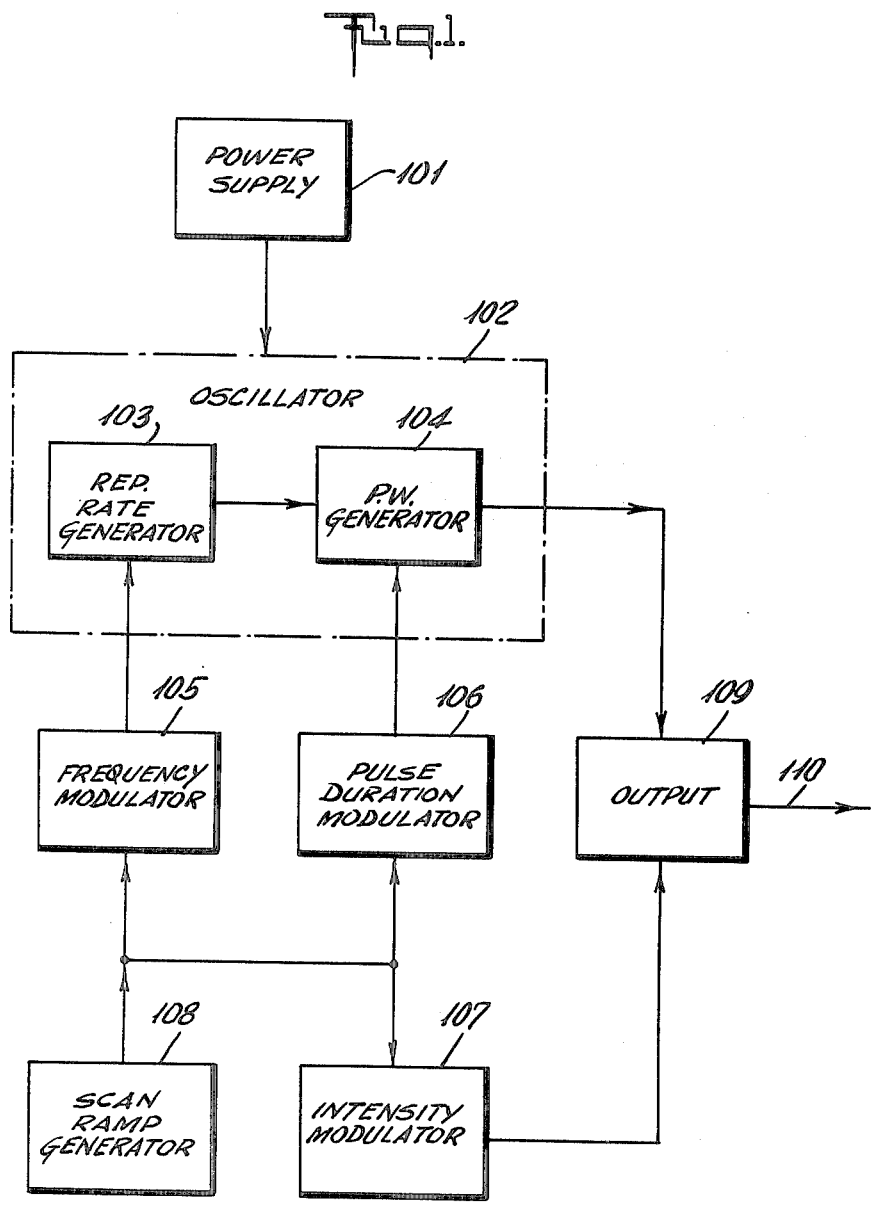

ELECTRONIC PAIN CONTROL WITH SCANNED OUTPUT PARAMETERS

TECHNICAL BACKGROUND

This invention relates to body function stimulating apparatus, and more particularly to apparatus and methods for controlling pain through the use of transcutaneous electrical nerve stimulation. Still more particularly, it relates to nerve stimulation apparatus and methods wherein the stimulating signals or pulses are varied through a succession of predetermined values or ranges, thereby achieving more effective pain control.

BACKGROUND ART

There is a long history of the employment of electrical shocks for various therapeutic needs. Centuries ago, electric eels were employed to provide the desired stimulation. Even to the present, it is believed by some to be beneficial to apply successive electrical shocks to the musculature, either to achieve muscular contractions, or for desired thermic action. See, for example, U.S. Pat. Nos. 2,936,762 and 3,261,358 to P. D. Bernard.

Electrical stimulation of human tissue has received its greatest acceptance, in recent years, with respect to electrical stimulation of the heart to stimulate pumping action, and to maintain adequate blood flow through the system. Further, increasing sophistication in semiconductor components and miniaturization thereof has allowed for corresponding sophistication in terms not only of the types of application of electrical stimulation, but furthermore to the ultimate controllability of the stimulating signals themselves. Present applications include stimulation of the carotid sinus, the urinary bladder, the intestines, the diaphragm, and the like. Further, there is ever increasing interest in the utilization of electrical stimulation of the nervous system to alleviate pain.

It is well known that living cells, both nerve and muscle cells, consist of an outer membrane containing an inner fluid of more or less structured water, containing various chemical ions such as potassium, calcium, and sodium. These ions are charged particles, and their concentration inside and outside of the cell results in an electrical and chemical polarization between the inside and outside of the cell wall. Muscular contraction and nervous communication is carried on by a depolarization of these cells. It is also well known that depolarization of these cells can be initiated by artificial electrical stimulation.

Predictably, different types of cells generally require correspondingly different types of electrical stimulating signals. For example, even considering nerve cells, there are different strength and duration requirements for electrical pulses which will effectively stimulate sensor (Class A afferent), motor (efferent), and noxous (Class C nociceptor) cells. Generally this results from the rather wide differences involved in the ranges of natural pulse repetition frequencies found in the various nerves. For example, the repetition frequency of the nervous signal stimulating the heart is of the order of 1 Hz, while the repetition frequency of pain provoked signals in the Class C fibres is on the order of 100 Hz.

There also exist differences in the parameters required for stimulation when a stimulating electrode is placed adjacent the cells that are being stimulated (e.g. the heart), as opposed to less proximate electrode placement, (e.g. electrodes at skin surface for stimulating a nerve several millimeters beneath the skin). Included amoung the critical output stimulation parameters are pulse repetition frequency, pulse duration, and pulse amplitude.

Accordingly, selection of parameters of a given stimulator will be influenced by the particular type of stimulation sought. For example, it is generally held that very short pulses will be relatively more effective in stimulating small fibres, than are relatively long pulses. Hence, when an electrode is placed within the proximity of more than one nerve in the same general area, and it is desired to stimulate one of them, some selectivity may be achieved by optimizing the stimulating parameters for that particular nerve. The field of optimization and selectivity is at this time, however, rather nascent.

It is known that feedback-type effects exist in the nervous system (often clinically referred to as "reverberation", "re-entry", "reciprocal rhythms", and the like). Among the approaches to electrical stimulation is the injection of a properly timed signal of proper amplitude, which appropriately alters the natural feedback operation. Correspondingly, the physiological and perceptive aspects of the nervous operation are altered or effectively canceled.

Further complicating the uniform administration of effective stimulation is the widespread diversity from person to person in physical nerve and muscle structure, and in associated electrical characteristics. These include not only the operational characteristics of the nerves, but also the locations of the nerves within the body and with respect to one another.

Disclosure of the Invention it is an object of the present invention to provide human body function stimulating apparatus which achieves relatively optimum effectiveness for a broad class of tissue or nerve types, and also accommodates a relatively broad range of variability in physiological structure of tissue and nerves.

The present invention is grounded on the proposition of a manifold approach to the application of electronic stimulation to physiologic systems, utilizing a scanning of various output parameters over respective predetermined ranges so that optimum parameter values are achieved at least a portion of the time that the stimuli are being provided. For example, if a given repetition frequency is optimum for a particular person for a particular type of nerve, although it is unlikely ever to effectively identify that optimum value, embodiments of the present invention will periodically achieve that value as the stimulation signal is scanned through a frequency range which on one hand is of minimal or negligible effect during portions of the scan, but which on the other does achieve the optimum for a clinically acceptable portion of the total time involved. Correspondingly, extensive and ultimately haphazard iterative fine tunings are obviated, and there also even results an accommodation to spontaneous variation of the optimum within the system over the clinical time period.

In an illustrative embodiment, a first oscillator means, having controllably variable pulse width, pulse amplitude, and pulse frequency parameters, provides the ultimate generation of the stimulating signals. A second, or scanning oscillator operates at least an order of magnitude slower than the first, and provides control for the variation of the output parameters, as desired. Hence, the periodicity of the scanning oscillator effectively establishes the frequency at which the undetermined optimum stimulating characteristic is reached. Preferably, the output of the scanning oscillator is a successively increasing and decreasing linear ramp signal. Separate pulse duration, pulse amplitude, and pulse frequency controls operate in response to the amplitude of the ramp from the scanning generator, and responsively thereto bring about a variation of the associated parameter at the first oscillator, each within respective clinically acceptable ranges in which the respective optimums are most likely to occur. In turn, the respective control functions are programmably variable, thereby adding further flexibility in terms of pulse rate, pulse duration, and pulse amplitude features.

BRIEF DESCRIPTION OF THE DRAWINGS

FIG. 1 shows a block diagrammatic version of an illustrative embodiment of the present invention.

BEST MODE FOR CARRYING OUT THE INVENTION

Figure 2A:
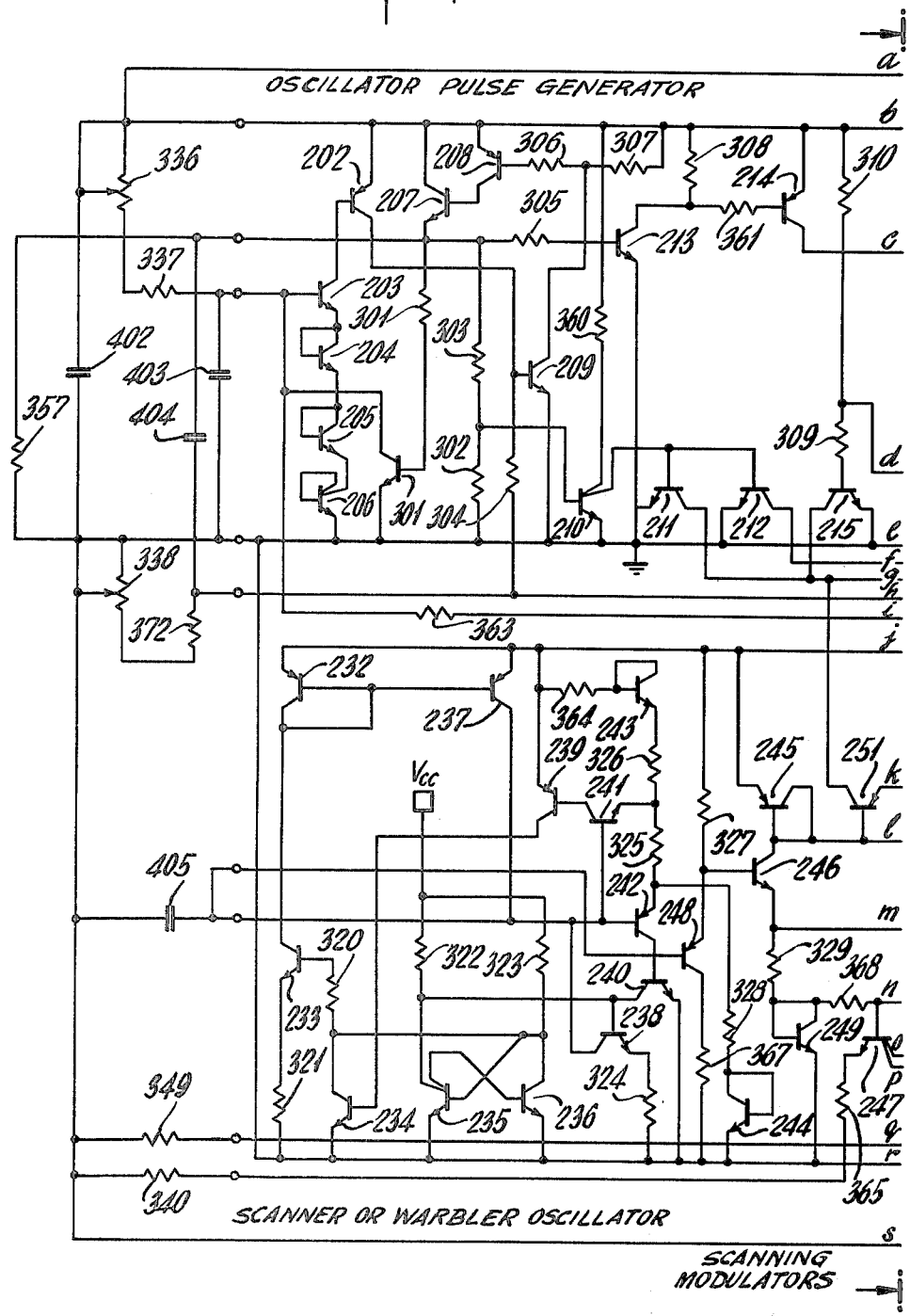
FIGS. 2A and 2B, when appropriately joined as shown, show a circuit schematic of a preferred embodiment of the present invention.

Referring first to FIG. 1, there is shown a block diagram of a transcutaneous nerve stimulation unit which embodies the principles of the present invention. A power supply 101 is understood suitably to deliver energizing voltage and current, as required, to the various other functional blocks of the unit. Generally, the power supply 101 is embodied as any of the numerous compact, long life dry cell batteries which are readily commercially available.

An output stage 109 furnishes a stimulation pulse signal at output terminal 110, which conventionally is coupled to one or more electrodes deposited on the patient, as is known in the art. From the standpoint of the principles of the present invention, the more important parameters with respect to the output signal at 110 are its pulse duration, pulse frequency, and pulse amplitude.

An oscillator 102 generates the basis of the stimulating signals, and couples them for suitable output amplification to the output stage 109. Functionally, the oscillator 102 is divided into two parts, a repetition rate generator 103 and a pulse width generator 104. In practice, the repetition rate generation and pulse width generation may not be completely discrete as shown in functional blocks 103 and 104 of FIG. 1, but from the standpoint of respective variation of each, they may be deemed functionally discrete as shown. Advantageously, the output signal from the oscillator 102 to the output stage 109, and in turn from the output terminal 110 to the patient, may involve a frequency range between 50 Hz and 150 Hz, with the width of each pulse varying between $20\mu$ and $150\mu$. Clearly, however, such parameters and the extremities of their ranges will be freely variable in accordance with the understanding of those of ordinary skill in the art, and in fact preferably are programmably variable in accordance with the principles of the present invention.

A scan ramp generator 108 produces a signal, based upon which the control of output pulse duration, pulse frequency, and pulse amplitude is maintained. Essentially, the scanning ramp generator 108 provides an output signal, advantageously defining successive increasing and decreasing ramps, the amplitude of which is the basis for respective frequency, pulse width, and pulse intensity modulation. Accordingly, the periodicity of the output signal from the scanning ramp generator 108 is substantially longer than the periodicity of the output from oscillator 102, preferably being at least an order of magnitude longer. In this fashion, the parameters of the output signal at 110 will be scanned through their respective ranges once for each half cycle of the signal from scanning ramp generator 108.

As shown in FIG. 1, the scanning ramp generator is coupled to the input terminals of a frequency modulator 105, a pulse width modulator 106, and an intensity modulator 107. In turn, the frequency modulator 105 is coupled to repetition rate generator 103 of oscillator 102, the pulse width modulator 106 is coupled to the pulse width generator 104 to oscillator 102, and the intensity modulator 107 is coupled to the output stage 109. Each of the modulators 105, 106, 107 provides a control signal, which in accordancd with the knowledge of those of ordinary skill in the art may be an analaog control voltage or a suitable digital word, responsive to which the associated parameter of the output signal is varied within its range. Hence, as the scanning ramp traverses between its minimum and maximum values, and vice versa, the frequency modulator 105 correspondingly provides a varying output control signal to the repetition rate generator 103 of oscillator 102, in turn producing a continuous frequency variation between range extremities for the output of oscillator 102, and in turn for the output signal at terminal 110. The pulse width modulator 106 operates similarly in response to the ramp from generator 108, causing pulse width generator 104 of oscillator 102 to provide continuous variation in pulse width, from one range extremity to the other, and similarly so for the output signal at 110. As shown in the drawing, the intensity modulator 107 controls the gain provided at the output stage 109, but it is understood that such modulation could also be accomplished directly at the output of oscillator 102. In any event, the pulse amplitude of the signal at 110 is thereby caused to be altered continuously between extremities of the selected pulse amplitude range.

In view of the disclosure set forth herein, it will be apparent that not all three output signal parameters of pulse frequency, pulse duration, and pulse intensity must be simultaneously scanned. Under certain circumstances, it may be desirable to have a single parameter, such as intensity, adjustable at a given amplitude, such as by the user or by a supervising nurse or a physician. In such instance, the intensity would thereby be established, while pulse frequency and pulse duration of the output signal would be scanned as set forth herein. Depending upon the skill of the user or the supervising physician or nurse at determining optimum parameters with respect either to frequency, duration, or intensity, it may even be desirable only to scan a single parameter, while the others remain fixed. Such applications, of course, also indicate the desirability of external programmability of the respective features, not only in terms of programming of the respective ranges, but furthermore in terms of establishing any parameter at a given fixed value.

For example, it may be desirable to maintain a relatively constant stimulation effectiveness, or a relatively uniform subjective sensation by the patient; in such events, it is desirable to have output current decreased while output pulse duration increases. Likewise, for other applications, it may be similarly desirable to maintain a constant total or average energy per unit time delivered to the patient, or to maintain specific average ranges, or below specified maximum values. Of course, the problem of establishing total or average energy values, or specific relative rates of change of specific parameters with respect to the others, is akin in difficulty to a determination of optimum values for a given parameter.

Nevertheless, certain general tendencies may be followed, to be further altered by those of ordinary skill in the art. Thus, one might choose component values such that pulse duration changes in one direction during the cycle, while pulse amplitude is changing inversely as the square root of the change in pulse duration. In such an instance, a one hundred percent increase in pulse duration would be accompanied by approximately a thirty percent decrease in pulse amplitude. Similarly, utilizing the principles of the present invention as set forth herein, adaptations may be made with respect to the various parameters and parameter ranges, taken alone or together, to accommodate stimulation at different nerves or different areas of entry of the stimulation. Moreover, as different frequencies and different phases are involved, it is to be expected that there will be increased probability of entering those reverberating loops found in some types of chronic pain, or of disturbing the coded pattern of impulses to the brain.

Figure 2B:
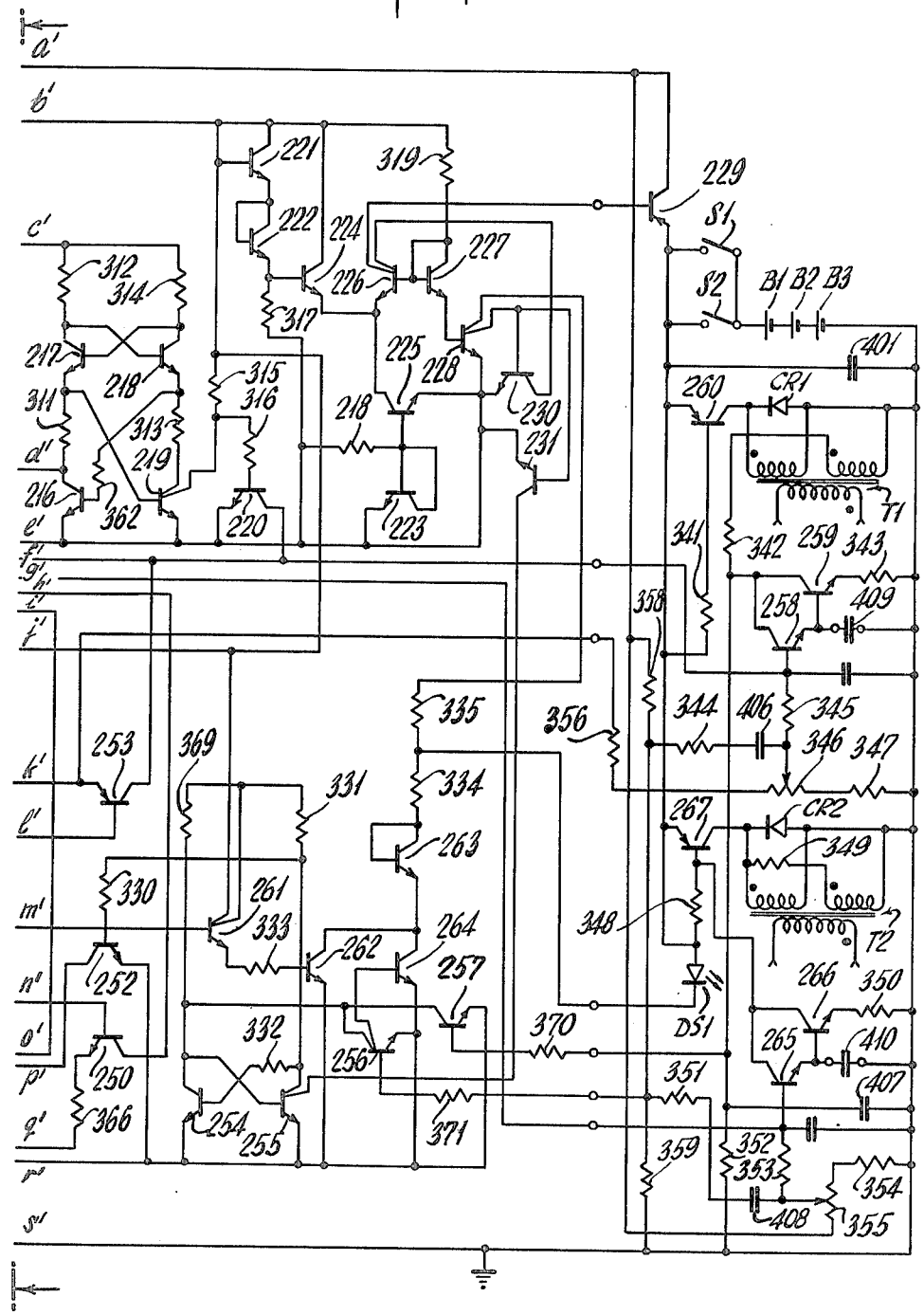

FIGS. 2A and 2B, when joined at connections A-A' through T-T' respectively, show a detailed circuit schematic of a preferred embodiment of the present invention. It will be understood that the embodiment of FIGS. 2A and 2B defines a complete, operational transcutaneous electrical nerve stimulating unit, including not only the aspects set forth in block diagrammatic form of FIG. 1, but also including other circuits and functional blocks suitable for incorporation in such a unit. Some of these functions and features are disclosed and claimed in a concurrently filed, co-pending application of W. Keller et al serial number (STM-12).

In FIG. 2B, batteries B1, B2, and B3 are series connected, and when switches S1 and S2 are closed, power is provided to the various circuitry. The unit of FIGS. 2A and 2B is a dual output unit, having respective output stages at transformers T1 and T2, with the secondaries of each transformer being connectable to suitable leads, in turn conveying the output stimulating pulses to electrodes disposed at appropriate places on the patient's body.

The embodiment of FIGS. 2A and 2B includes a voltage regulator function, with regulator transistor 229 having its emitter connected to the switches S1 and S2, and its base controlled by a differential amplifier formed by the emitter base junctions of transistors 226 and 224. The differential amplifier 226 and 224 senses the voltage attained by the difference between emitter-base voltage drops of transistors 221 and 222, off of the regulated voltage, $V_{CC}$, which is the voltage of the collector of regulating transistor 229 and the reference provided by the transistor VBE 228. Essentially, the voltage regulator function provides an independence of system parameters from battery voltage, as the batteries age and the battery voltages decrease.

The aspects of the FIGS. 2A-2B embodiment relating to the functions of oscillator 102 of FIG. 1 are located generally in the uppermost portion of FIG. 2A. That oscillator, which provides the essence of the output waveform in terms of pulse frequency and duration, is a free running, multivibrator type of circuit, wherein transistors 207, 208, and 209 are "on" when an output pulse is being produced, and are "off" during the interval between output pulses. Pulse duration is established by the operation of capacitor 404 in conjunction with resistors 338 and 372. Output pulse repetition frequency is controlled by the capacitor 403 in conjunction with resistors 336 and 337.

The output pulse signal from the oscillator is coupled to the output stages, located at the rightmost portion of FIG. 2B, via an alternating flip-flop including transistors 216 and 219, 217 and 218, and transistors 215 and 220. The flip-flop 216 and 219, in conjunction with steering transistors 217 and 218, provides an alternating pulse polarity as described in greater detail in the aforementioned currently filed co-pending application of W. Keller et al.

The scanning oscillator which fulfills the functions set forth with respect to scanning generator 108 of the FIG. 1 embodiment, is located at the lower leftmost portion of FIG. 2A. As described previously, the scanning ramp generator is an oscillator which provides a substantially lower frequency than that of the output oscillator 102, the purpose of the scanning oscillator being to provide for parameter changes for scanning at a repetition frequency preferably measured in the range of seconds (whereas the repetition frequency of the main oscillator will normally be on the order of tenths to one hundredths per second). The scanning oscillator includes transistors 235 and 236 connected in a monostable multivibrator configuration. Whenever transistor 235 is conducting, transistor 233 is also conducting to provide a current to transistors 232 and 237, with transistor 237 being a current source to capacitor 405. Conversely, if transistor 236 is conducting, transistor 238 acts as a current sink to the same capacitor, 405. Hence, whenever transistor 235 is conducting, the voltage on capacitor 405 is charging and changing positively, and when transistor 238 is conducting, the voltage on capacitor 405 is discharging and negative going. Transistor 241 determines the inflection point in the positive direction, and transistor 242 determines the inflection point in the negative direction. Accordingly, the voltage on capacitor 405 alternately rises and falls during the alternate two phases of each cycle of transistors 235 and 236, respectively. This upward and downward voltage on capacitor 405 is translated into corresponding upward and downward currents from transistors 247 and 250.

Transistor 247 modulates the charging current for capacitor 403, which in turn determines the repetition frequency of the basic oscillator. Thus, transistor 247 and its associated circuitry essentially fulfills the function attributed to the frequency modulator 105 of the FIG. 1 embodiment. In FIG. 2A, transistor 250 similarly modulates the pulse duration of the basic oscillator by modulating the charging current of capacitor 404. This corresponds to the operation of the pulse duration modulator 106 of FIG. 1.

Since the current at the emitter of transistor 246 is nearly identical to the collector current of transistor 246, there occurs a similar alternating up and down current available from transistors 251 and 253, to that previously described. Transistors 251 and 253 provide currents to the output circuits in FIG. 2B, so that the amplitude of pulses from transistors 260 and 267 is similarly modulated. The emitter resistances in transistors 247, 250, 251, and 253 are selected so that the amount of scan or warbling is determined. That is, resistors 365, 366, 349, 340, 346, 347, and 356 afford an opportunity for adjustability of the various modulation parameters.

Protection circuitry is provided at transistors 254, 255, 256, and 257 for sensing discontinuity at the output, such as might eventuate if the electrodes are detached from the patient. In order to avoid discomfort or danger to the patient, this aspect of the circuitry of FIGS. 2A and 2B provides an automatic disconnect function. Diode DS1 provides an indication to the user of the exercise of this feature.

The foregoing description of the embodiments of FIGS. 2A and 2B has focused largely on the aspects relating to the principles of the present invention, to wit, scanning the output parameters of pulse width, pulse frequency, and pulse amplitude. Operation of other detailed features of the circuitry will, in view of the schematic detail provided, be readily apparent to those of ordinary skill in the art. Furthermore, the aforementioned concurrently co-pending application of W. Keller et al contains further detail with respect to many of these features and functions.

It is to be understood that the foregoing has set forth illustrative and preferred embodiments of the present invention, but numerous alternative embodiments will occur to those of ordinary skill in the art without departure from the spirit or scope of the principles of the present invention. For example the output of the scan generator may assume any form desired by the designer, such as linear or specified non-linear shapes as may be known in the art.

What is claimed is:

1. A transcutaneous electrical nerve stimulator for pain control comprising: means for generating a pulse signal; respective means for continuous, automatic variation, through respective predetermined ranges, of the pulse signal parameters of output pulse width, and output pulse amplitude; and means, responsive to said respective means, for intermittently producing, for a given set of nerves, an output stimulation signal employing a signal amplitude—pulse width combination, and duration of that combination, which is adequate to produce requisite pain control effect.

2. A stimulator as described in claim 1 including means for further simultaneous variation of output pulse frequency, said means for producing selectively being further responsive to said means for variation of pulse frequency.

3. A stimulator as described in claim 1 wherein said means for producing varies pulse width and pulse amplitude in opposite senses thereby to maintain the average energy delivered to the nerves with an acceptable, predetermined range of total energy.

4. A transcutaneous electrical nerve stimulator for pain control comprising:
 a. first oscillator means for producing a signal having variable pulse rate, pulse amplitude, and pulse duration output parameter ranges within respective, effective nerve stimulating ranges;
 b. second oscillator means having a second output rate at least an order of magnitude slower than the rate of said first oscillator;
 c. control means, responsive to said second oscillator means, for selectively, independently varying the respective output parameters of said first oscillator means at said second rate; and
 d. output means, responsive to said control means for intermittently generating, for a given set of nerves, nerve stimulating signals employing a signal amplitude—pulse width combination, and duration of that combination, which is adequate to produce requisite pain control effect.

5. A stimulator as described in claim 4 wherein said second oscillator comprises means for generating respectively successive, substantially linear, increasing and decreasing half cycles at the output rate of said second oscillator.

6. A stimulator as described in claim 5 wherein said control means comprises means, responsive to the amplitude of the output signal of said second oscillator, for continuously and automatically varying the output rate of said first oscillator through a predetermined stimulation rate range.

7. A stimulator as described in claim 5 wherein said control means comprises means, responsive to the amplitude of the output signal of said second oscillator, for continuously and automatically varying the duration of output pulses from said first oscillator through a predetermined stimulation pulse duration range.

8. A stimulator as described in claim 5 wherein said control means comprises means, responsive to the amplitude of the output signal of said second oscillator, for continuously and automatically varying the amplitude of output pulses from said first oscillator through a predetermined stimulation pulse amplitude range.

9. A stimulator as described in claims 5, 6, or 7, wherein said first oscillator comprises at least one R-C second for establishing a given output parameter, and wherein said control means comprises means, responsive to said second oscillator, for altering the charging-discharging cycle of said R-C section, thereby correspondingly altering said given output parameter.

* * * * *